(12) United States Patent
Mateo Herrero

(10) Patent No.: US 9,468,207 B2
(45) Date of Patent: Oct. 18, 2016

(54) INSECTICIDE AND ACARICIDE PAINTS THAT INHIBIT CHITIN SYNTHESIS, REGULATE INSECT JUVENILE HORMONE AND REPEL ARTHROPODS, FOR CONTROLLING ENDEMIC DISEASES, PESTS AND ALLERGENS

(76) Inventor: Maria Pilar Mateo Herrero, Valencia (ES)

( * ) Notice: Subject to any disclaimer, the term of this patent is extended or adjusted under 35 U.S.C. 154(b) by 0 days.

(21) Appl. No.: 13/445,018

(22) Filed: Apr. 12, 2012

(65) Prior Publication Data

US 2013/0273129 A1    Oct. 17, 2013

(51) Int. Cl.
*A01N 25/04* (2006.01)
*A01N 25/28* (2006.01)

(52) U.S. Cl.
CPC .............. *A01N 25/04* (2013.01); *A01N 25/28* (2013.01)

(58) Field of Classification Search
CPC ............................ A01N 25/04; A01N 25/28
See application file for complete search history.

(56) References Cited

U.S. PATENT DOCUMENTS

| 5,931,994 A * | 8/1999 | Mateo Herrero | 106/15.05 |
|---|---|---|---|
| 2004/0134377 A1* | 7/2004 | Lee et al. | 106/15.05 |
| 2006/0029630 A1* | 2/2006 | Overman | 424/405 |
| 2009/0155394 A1 | 6/2009 | Overman | |

FOREIGN PATENT DOCUMENTS

| EP | 0 850 564 | 7/1998 |
|---|---|---|
| EP | 0 851 008 | 7/1998 |
| ES | 2 127 120 | 1/1999 |
| GB | 2 142 239 | 1/1985 |
| WO | 98/34481 | 8/1998 |
| WO | 2008/132067 | 11/2008 |

OTHER PUBLICATIONS

Supplementary European Search Report completed Mar. 6, 2013 in parallel European Application No. 09 85 0360.

* cited by examiner

*Primary Examiner* — Ali Soroush
(74) *Attorney, Agent, or Firm* — Wenderoth, Lind & Ponack, L.L.P.

(57) ABSTRACT

The present invention relates to insecticide and acaricide paints that inhibit chitin synthesis, regulate insect juvenile hormone and repel arthropods, for controlling endemic diseases, pests and allergens. The paints comprise at least the following compounds (in any combination): 1%-100% water, 0.0001%-20% insecticides, 0.0001%-20% chitin inhibitor, 0.0001%-20% juvenile hormone regulator, 1%-50% polymers, 0%-40% pigments, 0%-60% fillers, 0%-60% natural repellents, and 0.01%-20% stabilizers. The composition of the paints allows the active ingredients to be encapsulated in an aqueous polymer with or without the incorporation of fillers and pigments, and therefore the range of use thereof is increased.

12 Claims, 1 Drawing Sheet

INSECTICIDE AND ACARICIDE PAINTS THAT INHIBIT CHITIN SYNTHESIS, REGULATE INSECT JUVENILE HORMONE AND REPEL ARTHROPODS, FOR CONTROLLING ENDEMIC DISEASES, PESTS AND ALLERGENS

This application is a Continuation of International Application No. PCT/ES2009/070439.

FIELD OF THE ART

The invention refers to the field of paints, specifically to paints with insecticide and acaricide properties for controlling endemic diseases, pests and allergens.

STATE OF THE ART

It is known the existence in the market of paints with insecticide action (EP 871011308-2; FR 8601516; US 010300, CA 528968). However, these inventions have several significant drawbacks for the common use thereof:
- they contain obsolete active principles, which are not of the new generation,
- some of these active principles are currently prohibited in the European Union (e.g. organochlorine) because of their toxicity,
- active principles, as the traditional pyrethroids, which do not produce a residual character and have little effectiveness over time are used.

Application GB2142239 describes the use of insecticides in a formulation for paints and application US2006029630 describes the use of natural repellents for insects and arachnids in paints.

To solve these drawbacks new paints have been designed later, as those described in the Spanish patent ES2127120 for arthropods control. Said non-toxic and with residual character paints act as chitin synthesis inhibitors, one of the main components of the exoskeleton of arthropods. The composition of this type of paints comprises basically resin, pigment, fillers and active principles that are microencapsulated with the polymer of the resin itself in the manufacturing process.

On the basis of these considerations, the present invention, that also relates to insecticide and acaricide paints, entails a step forward against the state of the art given that it improves and broadens the arthropods control action claimed in the Spanish application no. 2127120.

The paints disclosed herein have novel variations in the composition, both in regards to the content by weight of the compounds used in the manufacture thereof and the incorporation of a) new active principles or insecticides, and b) new arthropod growth regulators that act controlling the juvenile hormone of the insects. In addition, these new paints have a repellent action of arthropods not described in the paints known until now, which allows their use in places where the use of products that incorporate insecticides or growth regulators of insects is prohibited.

BRIEF DESCRIPTION OF THE INVENTION

The present invention relates to insecticide and acaricide paints, that inhibit chitin synthesis, regulate insect juvenile hormone and repel arthropods, for controlling endemic diseases, pests and arthropods that act as allergens.

This invention relates to a new improved and expanded formula for controlling all kinds of arthropods (insects, mites). This control occurs both at the chemical level, as the formulation includes synthesis insecticides (pyrethroids, carbamates, neonicotinoids and phenylpyrazoles, in addition to organophosphates), and at the biological level, due to the incorporation of insect growth regulators (juvenile hormone analogues and chitin synthesis inhibitors).

In addition, a new active ingredient in the form of arthropod natural repellent is included which allows keeping them at a distance from the places where the formulation is applied; thus a repellent effect is achieved conferring new properties to the formulation and expanding the application possibilities of the formulation.

The composition of the paints allows the encapsulation of the active ingredients (insecticides, growth regulators and repellents) in an aqueous polymer with or without the addition of fillers and pigments in the same, which increases its range of use, so that they can be applied as conventional paints on walls and other rigid surfaces, or on other media that have already been scientifically tested as it is the case of fabrics.

The components involved in the technology of the paints described are essentially: a) copolymers of different types, such as VeoVa-type vinylic, acrylic, and in general polymers in aqueous base; b) active principles, such as insecticides, insect growth regulators and natural repellents; and c) the partial addition of fillers of the type of calcium carbonate and pigments with high luminosity and high chemical resistance, to be used as paint. It can also be provided only with the copolymer, without pigments or fillers, for its use as transparent emulsion.

DETAILED DESCRIPTION OF THE INVENTION

The insecticide and acaricide paints object of the present invention have been designed to control all kinds of arthropods due to their capacity to inhibit the chitin synthesis, regulate the insect juvenile hormone and repel arthropods. These insecticide and acaricide paints are characterized in that they comprise at least the following compounds:

|  | From | To |
|---|---|---|
|  | (in any combination) | |
| Water | 1% | 100% |
| Insecticides | 0.0001% | 20% |
| Chitin inhibitor | 0.0001% | 20% |
| Juvenile hormone regulator | 0.0001% | 20% |
| Polymers | 1% | 50% |
| Pigments | 0% | 40% |
| Fillers | 0% | 60% |
| Natural repellents | 0% | 60% |
| Stabilizers | 0.01% | 20% | wherein all the percentages are by weight with respect to the total weight of the composition, and they can be combined in any possible variation within the established ranges.

In a preferred embodiment, the composition of the paints is the following:

|  | % by weight of the total |
|---|---|
| Insecticides | 5% |
| Chitin inhibitor | 0.063% |
| Juvenile hormone | 0.063% |

-continued

| | % by weight of the total |
|---|---|
| regulator | |
| Polymers | 14% |
| Pigments | 10% |
| Fillers | 30% |
| Natural repellents | 5% |
| Stabilizers | 1% |
| Water | remaining % |

The insecticides used are synthesis actives specifically created for the formulation of insecticides for use in Public Health, Animal Health and Plant Health. Preferably, said insecticides are selected from a group consisting of organophosphates, carbamates, pyrethroids, neonicotinoids and phenylpyrazoles, or a combination thereof.

The action of organophosphate and carbamate is based on inhibiting the action of the enzyme acetylcholinesterase which is responsible for nerve transmission. In turn, pyrethroids also affect the nervous system of the insect, but acting as dissociative of the axonal membrane, keeping open the sodium channels of said membrane. Neonicotinoids act on the central nervous system of the insects, causing an irreversible blockade of the postsynaptic nicotinergic acetylcholine receptors. Besides, phenylpyrazoles block the chlorine channels regulated by the γ-aminobutiric acid (GABA) in the neurons of the insects.

These groups have insecticides which act by contact, ingestion and inhalation and they do it on the different development stages of insects and arachnids, although the egg stage is especially resistant to their action.

Preferably, organophosphate insecticides are selected from a group consisting of Diazinon, chlorpyrifos, methyl-chlorpyrifos, malathion, trichlorfon, dimethoate, dichlorvos, methamidophos, acetate, parathion, fenitrothion, fenthion and azinphos-methyl, or a combination thereof. Also preferably carbamates are selected from a group consisting of methomyl, aldicarb, oxamyl, thiodicarb, methiocarb, propoxur, bendiocarb, carbosulfan, fenoxycarb, pirimicarb, indoxacarb, alanycarb and furathiocarb, or a combination thereof. In turn, pyrethroids are preferably selected from a group consisting of allethrin, d-allethrin, alpha-cypermethrin, cypermethrin, permethrin, tetramethrin, bioallethrin, fenvalerate, bifenthrin, cyfluthrin, deltamethrin, prallethrin, acenathrin, imiprothrin, lambda-cyhalothrin, gamma-cyhalothrin and etofenprox, or a combination thereof. In another preferred embodiment, neonicotinoids are selected from a group consisting of imidacloprid, acetamiprid, thiamethoxam, nitenpyram, clothianidin, dinotefuran and thiacloprid, or a combination thereof. Phenylpyrazoles are selected from fipronil and endosulfan, or a combination thereof, preferably.

The chitin synthesis inhibitors are framed within the so-called growth regulator insecticides (IGRs), and are preferably selected from a group consisting of flufenoxuron, hexythiazox, diflubenzuron, hexaflumuron and triflumuron, or a combination thereof.

These inhibitors have the following way of action: the insects are coated by a rigid exoskeleton, the integument, which provides them protection and prevents the loss of water, allowing their survival. Insects, in order to be able to develop and due to the rigidity of the aforementioned integument, must grow in a discontinuous way. For this, they periodically get rid of the integument and create a larger new one. This process is known as "molting".

The application of the chitin synthesis inhibitors used in the paint gives rise to a process capable of inhibiting the chitin production mechanism, the main component of the integument. By preventing its production, the formation of a new integument is blocked and as a result the molting process does not take place, whereby its development and, therefore, its existence is unviable.

The activity of the product affects all the stages of sensitive insects although in a different way. It affects eggs of some species when they are deposited on the vegetable parts of treated plants or when the same are treated once deposited. Eggs can develop, but the larvae from the same are unable to emerge or die shortly thereafter. It affects the larval stages by preventing the molting, which leads to the appearance of symptoms such as: double cephalic capsule, ballooning of the thorax, and displaced or deformed jaws. As a result of the inability to molt, the larvae die since they are not able to evolve to subsequent stages. Due to the aforementioned deformations, they are unable to feed, what makes their survival impossible. The larvae exposed to sub lethal doses of the product can "pupate" but they do not produce viable adults or give rise to adults who lay fewer eggs than normal. It affects the adults by reducing their fertility.

As for the juvenile hormone analogues, they are selected preferably from a group consisting of pyriproxyfen, fenoxycarb, hydroprene and methoprene, or a combination thereof. This type of compounds acts by maintaining high the levels of juvenile hormone (JH) in the insect. The molting process in the insects is controlled by two hormones: β-ecdysone and juvenile hormone. The normal development of the insect depends on a precise adjustment of the JH concentrations at each stage. A disturbance in the relationship between the JH concentration and the development stage leads to abnormal development. When the JH levels are lower than those of β-ecdysone the molting process begins.

To prevent the maturation of the insects, the juvenile hormone and its synthetic analogues are non-toxic and environmentally sensitive means to fight the insects which are very difficult to develop resistance. The JH analogues do not reduce the population immediately as classic insecticides do, but control is achieved in approximately one generation.

The natural insects repellents used in the manufacture of the paints are selected preferably from a group consisting of citronella, lavender oil, garlic extract, eucalyptus oils, thyme oils, basil and others extracted from plants with insect repellent properties, or a combination thereof.

Natural insects repellents were one of the first strategies for fighting or preventing the presence of insects within homes. Initially leaves and flowers of plants were used, then essential oils were extracted from these plants and, later, these oils were included in fuels, as wax and petroleum, to release the repellent substances to the environment.

Synthesis insecticides, insect growth regulators and natural insects repellents are incorporated into the formulation by the micro-encapsulation process of a polymer which is detailed below.

The structure of the microcapsule is an active core and a frame that surrounds the first. The production process is complex, since the active substances (the insecticides, the insect growth regulators and the insects repellents) are introduced in the polymer nature matrix or wall system, achieving, due to the polymer, a gradual release of the active agents, inserted depending on the specific application needs of the substrate on which the microcapsules are deposited. The microcapsule formation is a chemical process, both with the copolymers and the actives mixture jointly, and the micro-encapsulation of the polymers with the juvenile growth hormone regulators, the chitin synthesis inhibitors or the repellents, all of them together or separately in the polymer matrix in the encapsulation, resulting in a suspension of microcapsules ranging between one and several hundred micrometers. The progressive and controlled release of the microencapsulated actives is achieved due to the nature of the polymer coating them. It has an easy, durable, resistant to rain and effective application.

With regard to the other elements that make up the paints object of the present invention, the resins used are preferably polymers in aqueous base, and more preferably vinyl or acrylic copolymers or a combination thereof. Preferably, vinyl copolymers are of the VeoVa type.

The fillers of the paints are preferably selected from a group consisting of calcium and magnesium carbonates, or a combination of both. The pigments are preferably of the titanium dioxide type. The composition included in the patent allows the use or not of fillers and pigments which greatly diversifies its range of application; as it can be applied as a conventional paint with brush, roller or "airless"-type spray gun on walls and other rigid surfaces or, in the case of not including fillers or pigments in the formulation it can be applied by spraying on other supports as it is the case of all kinds of fabrics—canvas, curtains, carpets, rugs, clothes.

Finally, the stabilizers used are those common in a plastic paint, being preferably selected from a group consisting of sodium benzoate, sodium hexametaphosphate and sodium nitrite, or a combination thereof, among others. In short, the present invention provides a new methodology for controlling arthropods-pests, wherein a high efficiency over a wide range of arthropods as cockroaches, mosquitoes, flies, bugs, scorpions, mites and spiders is achieved through a single application. The formulation acts primarily by contact, but it also does it by inhalation.

DESCRIPTION OF THE FIGURE

FIG. 1. Image of the structure of the microcapsule. The structure of the microcapsule consists of an active core surrounded by a frame. The production process is complex, since the active substances (the insecticides, the insect growth regulators and the insects repellents) are introduced in the polymer nature matrix or wall system, achieving, due to the polymer, a gradual release of the active agents, inserted depending on the specific application needs of the substrate on which the microcapsules are deposited.

The invention claimed is:

1. An insecticide and acaricide paint composition that inhibits chitin synthesis, regulates juvenile hormone of insects and repels arthropods, for controlling endemic diseases, pests and arthropods acting as allergens, comprising at least the following compounds:

insecticides, in a percentage comprised between 0.0001% and 20%, including both limits, selected from pyrethroids;

chitin inhibitor, in a percentage comprised between 0.0001% and 20%, including both limits, juvenile hormone analogues, in a percentage comprised between 0.0001% and 20%, including both limits, polymers, in a percentage comprised between 1% and 50%, including both limits, pigments, in a percentage comprised between 0% and 40%, including both limits, fillers, in a percentage comprised between 0% and 60%, including both limits, natural repellents in a percentage comprised between 0% and 60%, including both limits, stabilizers, in a percentage comprised between 0.01% and 20%, including both limits, and water, in a percentage between 1% and a quantity sufficient to complete 100%, wherein all percentages are by weight with respect to a total weight of the composition, and the compounds can be combined in any possible variation with the established ranges, and wherein the insecticides, the chitin inhibitor, the juvenile hormone analogues and the natural repellents are separately microencapsulated.

2. The paint composition according to claim 1, comprising the following composition:

insecticides, selected from pyrethroids: 5%, chitin inhibitor: 0.063%, juvenile hormone analogues: 0.063%, polymers: 14%, pigments: 10%, fillers: 30%, natural repellents: 5%, stabilizers: 1% and, water: remaining percentage, wherein all percentages are by weight with respect to the total weight of the composition.

3. The paint composition according to claim 1, wherein the pyrethroids are selected from the group consisting of allethrin, d-allethrin, alpha-cypermethrin, cypermethrin, permethrin, tetramethrin, bioallethrin, fenvalerate, bifenthrin, cyfluthrin, deltamethrin, prallethrin, acenathrin, imiprothrin, lambda-cyhalothrin, gamma-cyhalothrin, etofenprox, and a combination thereof.

4. The paint composition according to claim 1, wherein the chitin inhibitor is selected from the group consisting of flufenoxuron, hexythiazox, diflubenzuron, hexaflumuron, triflumuron, and a combination thereof.

5. The paint composition according to claim 1, wherein the juvenile hormone analogues are selected from the group consisting of pyriproxyfen, fenoxycarb, hydroprene, methoprene, and a combination thereof.

6. The paint composition according to claim 1, wherein the natural repellents are selected from the group consisting of citronella oil, lavender oil, garlic extract, eucalyptus oils, thyme oils, basil, others extracted from plants with insect repellent properties, and a combination thereof.

7. The paint composition according to claim 1, wherein the polymers are resins in aqueous base.

8. The paint composition according to claim 7, wherein the polymers are vinyl or acrylic copolymers or a combination thereof.

9. The paint composition according to claim 8, wherein the vinyl copolymers are VeoVa vinyl copolymers.

10. The paint composition according to claim 1, wherein the fillers are selected from the group consisting of calcium, magnesium carbonates, and a combination of both.

11. The paint composition according to claim 1, wherein the pigments are titanium dioxide pigments.

12. The paint composition according to claim 1, wherein the stabilizers are at least one selected from the group consisting of sodium benzoate, sodium hexametaphosphate and sodium nitrite.

* * * * *